United States Patent

Shinozaki et al.

Patent Number: 5,192,774
Date of Patent: Mar. 9, 1993

[54] SUBSTITUTED ACETAMIDE DERIVATIVES, PROCESS FOR THEIR PREPARATION AND ANTIULCER DRUG CONTAINING SAME

[75] Inventors: Katsuo Shinozaki; Katsuyuki Ishii, both of Konan; Ikuo Ueda, Toyonaka, all of Japan

[73] Assignee: Zeria Pharmaceutical Co., Ltd., Tokyo, Japan

[21] Appl. No.: 465,238

[22] PCT Filed: Jul. 4, 1989

[86] PCT No.: PCT/JP89/00670

§ 371 Date: May 7, 1990

§ 102(e) Date: May 7, 1990

[87] PCT Pub. No.: WO90/00544

PCT Pub. Date: Jan. 25, 1990

[30] Foreign Application Priority Data

Jul. 5, 1988 [JP] Japan ................. 63-165822

[51] Int. Cl.$^5$ ................ A01N 43/40; C07D 211/32; C07D 211/60

[52] U.S. Cl. ................ 514/315; 514/326; 514/331; 514/385; 514/422; 514/428; 546/192; 546/210; 546/230; 546/233; 548/517; 548/314.7

[58] Field of Search ............. 546/233, 192, 210, 230; 548/300, 517; 514/385, 326, 315, 331, 422, 428

[56] References Cited

U.S. PATENT DOCUMENTS 4,837,316 6/1989 Sekine et al. .............. 546/233

Primary Examiner—C. Warren Ivy
Assistant Examiner—Raymond Covington
Attorney, Agent, or Firm—Oblon, Spivak, McClelland, Maier & Neustadt

[57] ABSTRACT

A substituted acetamide derivative of general formula (I):

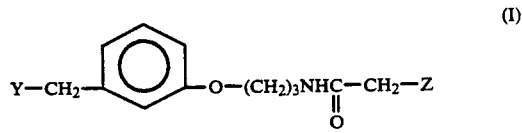

[in which Y represents as piperidino group, 1-pyrrolidinyl group or 3-hydroxy-1-pyrrolidinyl group, and Z represents a group selected from the group consisting of (a) to (e): (a) a cyano group,

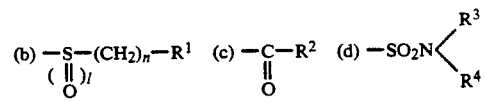

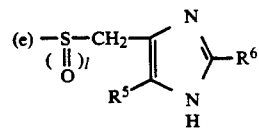

its salts, its cyclodextrin inclusion compounds and antiulcer drugs comprising them as their active ingredient are disclosed. Compounds (I) have excellent antiulcer actions and are highly safe, thus the antiulcer drugs containing the compounds are useful as a preventive and curative medicine against acute and chronic gastric ulcers, duodenal ulcers and gastric hyperacidities.

9 Claims, No Drawings

SUBSTITUTED ACETAMIDE DERIVATIVES, PROCESS FOR THEIR PREPARATION AND ANTIULCER DRUG CONTAINING SAME

DESCRIPTION

Technical Field

This invention relates to novel substituted acetamide derivatives, their cyclodextrin inclusion compounds, a process for their preparation and antiulcer drugs containing the same.

Background Art

The developmental mechanism of a peptic ulcer is complicated because it is influenced by a variety of factors. Peptic ulcers are considered to be caused when the balance between aggressive factors (inhibition of gastric acid secretion) and protective factors (cytoprotective action) for the tunica mucosa of the stomach is lost. It is therefore effective preventive or curative means to inhibit the secretion of the gastric acid serving as an aggressive factor.

Hitherto, in the clinical field, anticholinergic agents and histamine $H_2$ receptor blockers such as cimetidine have widely been used as effective agents for suppressing the gastric acid secretion.

However, the anticholinergic agents are accompanied by side-effects such as the suppression of the discharge movement of the stomach, thirst, mydriasis and inhibition of perspiration. What is worse, they cannot effectively prevent the aggravation of the ulcer nor prevent the relapse of it even when they are used in such amounts that would substantially inhibit the gastic acid secretion. Meanwhile, cimetidine causes undesirable side effects such as central actions and an antiandrogen effect. Furthermore, a problem arises in that the protective factors in the tunica mucosa function less if cimetidine is administered for a long term. As a result, it causes the relapse of the ulcer when the administration of cimetidine has been stopped.

Therefore, a desire has been arisen for an improved antiulcer drug capable of effectively controlling the secretion of gastric acid which serves as an aggressive factor, and having a protective factor potentiation action (cytoprotective action).

The inventors have studied for the purpose of finding an improved antiulcer compound capable of effectively controlling the secretion of gastric acid which serves as an aggressive factor, and having a protective factor potentiation action (cytoprotective action). As a result, the present invention was achieved, in which a substituted acetamide derivative of formula (I), its salts, and inclusion compounds thereof in cyclodextrin were found to meet the above objects.

DISCLOSURE OF INVENTION

According to the present invention, there is provided substituted acetamide derivatives, salts thereof, inclusion compounds obtained by causing said substituted acetamide derivatives or the salts thereof included in cyclodextrin and antiulcer drugs comprising them as active ingredient, the substituted acetamide derivative being represented by the following general formula (I):

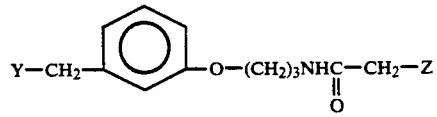
(I)

[in which Y represents a piperidino group, 1-pyrrolidinyl group, or 3-hydroxy-1-pyrrolidinyl group, and Z represents a group selected from the group consisting of (a) to (e):

(a) a cyano group;
(b) a group expressed by

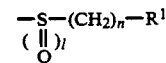

(in which l represents an integer from 0 to 2, n represents an integer from 1 to 3, $R^1$ represents a hydroxy group, 1,2-dihydroxyethyl group, 1-hydroxyethyl group, 2-phenyl-1-hydroxyethyl group, 2-hydroxyethoxy group, lower alkoxycarbonyl group, 2,2-dimethyl-1,3-dioxolan-4-yl group, or a lower acyloxymethyl group);

(c) a group expressed by

(in which $R^2$ represents an amino group, lower alkylamino group, di(2-hydroxyethyl)amino group, lower alkyl group, or a lower alkoxy group);

(d) a group expressed by

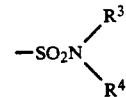

(in which $R^3$ and $R^4$ respectively represent a hydrogen atom, or a lower alkyl group);

(e) a group expressed by

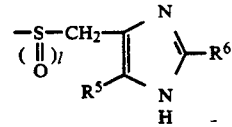

(in which l represents an integer from 0 to 2, and $R^5$ and $R^6$ respectively represent a hydrogen atom or a lower alkyl group).

BEST MODE OF THE INVENTION

The lower alkyl group of compound (I) according to the present invention is exemplified by a straight or a branched chain alkyl group having 1 to 6 carbon atoms, preferably methyl, ethyl, n-propyl, isopropyl, n-butyl, isobutyl and tert-butyl groups. The lower alkozy group is exemplified by a straight or a branched chain alkoxy group having 1 to 6 carbon atoms, preferably methoxy, ethoxy, n-propoxy, isopropoxy, n-butoxy, isobutoxy and tert-butoxy groups. The lower acyl group is exemplified by a straight or branched chain alkanoil group having 2 to 7 carbon atoms, preferably acetyl, propionyl, n-butyryl and isobutyryl groups. The halogen atom is exemplified by fluorine atoms, bromine atoms, chlorine atom and iodine atom, among which bromine atom and chlorine atom are preferred.

The salts of compound (I) according to the present invention are those which are medicinally accepted, which include salts of organic acids such as acetic acid, maleic acid, citric acid, oxalic acid, fumaric acid and hybenzoic acid; salts of inorganic acid such as hydrochloric acid, sulfuric acid and nitric acid and bromic acid.

Compounds (I) according to the present invention can be prepared, for example, by any of the following preparation methods A to E.

<PREPARATION METHOD A>

$$Y-CH_2-\underset{(II)}{\underset{|}{\bigcirc}}-O-(CH_2)_3NH\underset{\underset{O}{\|}}{C}-CH_2-X +$$

$$\underset{(III)}{A-Za} \longrightarrow$$

$$Y-CH_2-\underset{(Ia)}{\underset{|}{\bigcirc}}-O-(CH_2)_3NH\underset{\underset{O}{\|}}{C}-CH_2-Za$$

[in which X represents a halogen atom, A represents a hydrogen atom, potassium atom or a sodium atom, Za represents (a) a cyano group or (b') a group expressed by $-S-(CH_2)_n-R^1$ (in which n and $R^1$ respectively represent the same meanings as described before].

That is, the compounds of general formula (Ia) according to the present invention can be prepared by reacting an acetamide derivative of general formula (II) and a compound of general formula (III).

It is preferable that the reaction according to preparing method A be performed in a solvent which does not influence the reaction. The solvent is exemplified by: alcohol such as methanol, ethanol and propanol; amides such as dimethylformaldehyde and diethylformaldehyde; ethers such as tetrahydrofuran and dioxane; hydrocarbon halides such as dichloromethane and chloroform; aromatic hydrocarbons such as benzene, toluene and xylene; acetonitryl; and dimethyl sulfoxide. Reaction temperature and reaction time may be changed according to the starting materials, and generally, 0° to the reflux temperature under atmospheric pressure.

<PREPARATION METHOD B>

$$Y-CH_2-\underset{(IV)}{\underset{|}{\bigcirc}}-O-(CH_2)_3NH_2 + \underset{(V)}{B-Zb} \longrightarrow$$

-continued $$Y-CH_2-\underset{(Ib)}{\underset{|}{\bigcirc}}-O-(CH_2)_3NH\underset{\underset{O}{\|}}{C}-CH_2-Zb$$

[in which, B represents a lower alkoxycarbonylmethyl group and Zb represents a group selected from (a) to (e):

(a) a cyano group;
(b) a group expressed by $$-\underset{(\underset{O}{\|})_l}{S}-(CH_2)_n-R^{1a}$$

(in which l represents an integer from 0 to 2, n represents an integer from 1 to 3 and $R^{1a}$ represents a hydroxy group, 1,2-dihydroxyethyl group, 1-hydroxyethyl group, 2-phenoxy-1-hydroxyethyl group, 2-hydroxyethoxy group or 2,2-dimethyl-1,3-dioxolan-4-yl group), (c) a group expressed by $$-\underset{\underset{O}{\|}}{C}-R^{2a}$$

(in which $R^{2a}$ represents an amino group, a lower alkyl amino group, di(2-hydroxyethyl)amino group or a lower alkoxy group), (d) a group expressed by $$-SO_2N\underset{R^4}{\overset{R^3}{<}}$$

(in which $R^3$ and $R^4$ respectively represent a hydrogen atom or a lower alkyl group), (e) a group expressed by $$-\underset{(\underset{O}{\|})_l}{S}-CH_2\underset{R^5}{\overset{}{\underset{}{\Big[}}}\underset{\underset{H}{N}}{\overset{N}{\Big\rangle}}-R^6$$

(in which l, $R^5$ and $R^6$ respectively represent a hydrogen atom or a lower alkyl group).

That is, a compound according to the present invention of general formula (Ib) can be prepared by reacting an amine derivative of general formula (IV) and a compound of general formula (V).

It is preferable that the reaction in preparation method B be performed in a solvent which does not influence the reaction. The solvent is exemplified by: alcohol such as methanol, ethanol and propanol; amides such as dimethylformamide and diethylformamide; ethers such as tetrahydrofuran and dioxane; acetonytryl; dimethylsulfoxide; hydrocarbon halides such as dichloromethane and chloroform; and aromatic hydrocarbons such as benzene, toluene and xylene. Reaction temperature and reaction time may be changed according to the starting materials, and generally, 0° to the reflux temperature under atmospheric pressure.

PREPARATION METHOD C

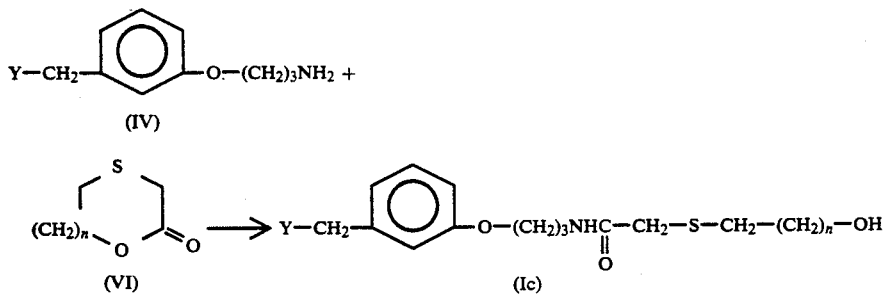

[in which n and Y respectively represent the same meanings as described before].

That is, the compound of general formula (Ic) according to the present invention can be prepared by reacting an amine derivative of general formula (IV) and a compound of general formula (VI).

The reaction according to preparation method C is performed by using a non-proton solvent which does not influence the reaction, the solvent being exemplified by: aromatic hydrocarbons such as benzene, toluene and xylene; ethers such as tetrahydrofuran and dioxane; and amides such as dimethylformamide and diethylformamide. Reaction temperature and reaction time may be changed according to the starting materials, and generally, 0° C. to the reflux temperature under atmospheric pressure.

PREPARATION METHOD D

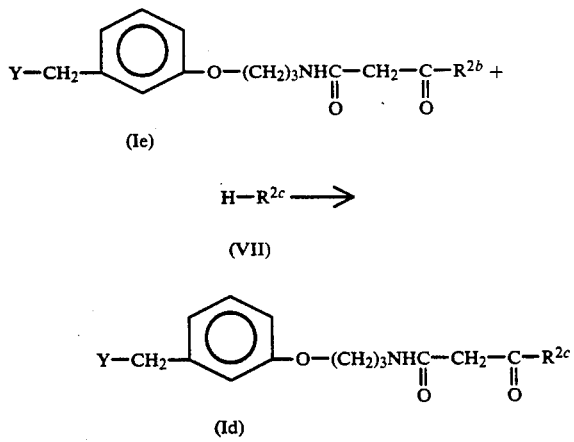

[in which $R^{2b}$ represents a lower alkoxy group, $R^{2c}$ represents an amino group, a lower alkylamino group and di(2-hydroxyethyl)amino group, and Y represents the same meaning as described before].

That is, a compound of general formula (Id) according to the present invention can be prepared by reacting a compound of general formula (Ie) and a compound of general formula (VII).

The reaction according to the preparation method D is performed by using a solvent which does not influence the reaction, the solvent being exemplified by: alcohol such as methanol, ethanol and propanol; aromatic hydrocarbons such as benzene, toluene and xylene; amides such as dimethylformamide and diethylformamide; ethers such as tetrahydrofuran and dioxane; hydrocarbon halides such as dichloromethane and chloroform. Reaction temperature and reaction time may be changed according to the starting materials, and generally, 0° to the reflux temperature under atmospheric pressure.

PREPARATION METHOD E

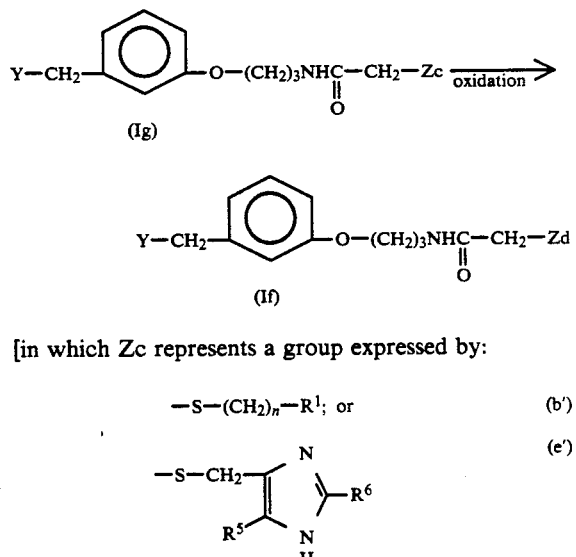

[in which Zc represents a group expressed by:

$-S-(CH_2)_n-R^1$;  or    (b')

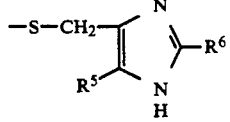    (e')

(in which n, $R^1$, $R^5$ and $R^6$ respectively represent the same meaning as described before), and Zd represents a group expressed by:

$-\underset{\underset{O}{(\|)_q}}{S}-(CH_2)_n-R^1$    (b")

or

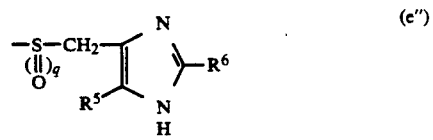    (e")

(in which q represents an integer 1 or 2; n, $R^1$, $R^5$ and $R^6$ respectively represent the same meanings as described before), and Y represents the same meaning as described before].

That is, a compound of general formula (If) according to the present invention can be prepared by oxidizing a compound of general formula (Ig).

In preparation method E, a conventional oxidation reaction for thioether compounds may be applied, wherein an oxidizing agent is reacted in a suitable solvent. The solvent is exemplified by: alcohol such as ethanol; aromatic hydrocarbons such as benzene, toluene and xylene; ethers such as tetrahydrofuran and dioxane; hydrocarbon halides such as chloroform and methylen chloride. The oxidizing agent is exemplified by organic peroxides such as periodic acid, hydrogen peroxide, methachloroperbenzoic acid, perphhalic acid and permaleic acid. For example, the oxidation to sulfinyl of q=1 may be performed by reacting periodic acid in hydrated alcohol, while the oxidation to sulfinyl of q=2 may be performed by reacting hydrogen peroxide in organic acid.

The inclusion compounds of compound (I) according to the present invention can be prepared by a usual method by using cyclodextrin such as α-cyclodextrin, β-cyclodextrin and γ-cyclodextrin. In the case where the compound according to the present invention is a water insoluble compound and/or an amorphous compound, it can be converted into a water soluble compound and/or a crystallizable compound by forming inclusion compounds of cyclodextrin, which is advantageous for the manufacture of medicines.

The toxicity and anti-ulcer activity of compounds (I) according to the present invention will be described hereinbelow.

The aggressive factor inhibition action was evaluated from the effects on the gastric acid secretion of anesthesia fistula rats by histamine, while the protective factor potentiation action was evaluated from the effects observed in a hydrochloric acid-ethanol ulcer model. In the Tables, the column of test compounds indicates Example numbers where the compounds are prepared.

(1) Effects on Gastric Acid Secretion of Anesthesia Fistula Rat by Histamine:

Male SD rats (Japan Charles River Co., Ltd.) each weighing 180 to 200 g were fasted for 24 hours before celiotomy with etherrization. A feeding tube (fr. 3.5) for injecting test medicines was inserted into the duodenum, and the pylorus was ligatured. A polyethylene tube (inner diameter: 7 mm) was used in the anterior stomach and gastric fistula was performed. After washing the inside of the stomach with heated physiological salt solution (37° C.) several times, the body was closed. A tube with a fin was inserted into the caudal vein and was fastened with a tape and it was connected to a infusion pump (Harvard). The rats were enclosed in a KN Ballman II cage (Natsume Seisakusho). Gastric juice flowed from the fistula was collected with a mess-cylinder every one hour. Starting form one hour after the operation, histamine was continuously injected at a rate of 1.4 ml/hour through the caudal vein. Then, test compounds suspended in 0.5% sodium caboxy methyl cellulose (Na-CMC) were administered one hour after the start of the histamine injection. The gastric juice thus extracted in a period from one hour after the administration of the chemical to four hours after that was titrated by using an automatic titration aparatus (Kyoto Electronic) with 0.1N NaOH to adjust pH 7, and the quantity of the gastric juice was measured to obtain the total acid output.

The inhibition rate (%) of the gastric acid secretion was calculated form the following equation, which results are shown in Table 1.

Inhibition Rate (%) of Gastric Acid secretion =

$$1 - \frac{\text{total acid output of test compound group}}{\text{total acid output of control group}}$$

TABLE 1

Effects on Gastric Acid Secretion of Anesthesia Fistula Rat by Histamine

| | Dose (mg/kg) | Gastric acid secretion inhibition effect (%) |
|---|---|---|
| Test Compounds | | |
| Example 2 | 30 | 79.5 |
| 7 | 30 | 59.4 |
| 8 | 30 | 70.9 |
| 12 | 30 | 55.4 |
| Comparative Compounds | | |
| Cimetidine | 30 | 32.3 |
| Roxatidine | 30 | 68.8 |

As shown in Table 1, the compounds according to the present invention effectively inhibited the gastric acid secretion of anesthesia fistula rat, which was caused by the histamine stimulus.

(2) Hydrochloric Acid-Ethanol Ulcer Test

Male SD rats each weighing 170 to 190 g were fasted for 24 hours, and 1 ml of 150 mM hydrochloric acid-60% ethanol was orally administered to each rat. After one hour, rats were clubbed to death, and the stomach was extracted. 10 ml of 2% formalin solution was applied to the stomach for fixing for 10 minutes. The length (mm) of the injuries in the tunica mucosa taken place in the glandular stomach was measured under a stereoscopic microscope. The total length of the injuries of the individual was taken as the ulcer index.

Test compounds or control (1% Na-CMC) were orally administered in an amount of 0.5 ml/100 g, 30 minutes before the administration of hydrochloric acid-ethanol.

The ulcer inhibition rate was calculated by the following equation, which results are shown in Table 2.

Ulcer inhibition rate (%) =

$$\left(1 - \frac{\text{Ulcer index of test compound group}}{\text{Ulcer index of control group}}\right) \times 100$$

TABLE 2

Effects on Ulcer Formation Caused by Hydrochloric Acid-Ethanol

| | Dose (mg/kg) | Ulcer Inhibition Rate(%) |
|---|---|---|
| Test Compounds | | |
| Example 2 | 100 | 72.5 |
| Comparative Compounds | | |
| Cimetidine | 100 | 22.7 |
| Roxatidine | 100 | 69.4 |

As shown in Table 2, the compounds according to the present invention effectively inhibit the ulcer formation on an ulcer model caused by hydrochloric acid-ethanol, thus have a preventive factor potentiation action.

(3) Toxicity test

The compounds according to Examples 2, 7, 8 and 12 were respectively suspended in 3% gum arabic solution and continuously, forcedly and orally administered to three ICR:Crj 5 week old male mice for 14 days at a dose of 500 mg/kg/day. No rat died and weight loss was not observed. In an acute toxicity test by an oral administration of the compounds, the $LD_{50}$ value of the compound according to Example 2 was 2383 mg/kg, and the $LD_{50}$ value caused form Roxatidine was 755 mg/kg.

As described above, it has been confirmed that the compounds according to the present invention are excellent antiulcer agents having both the aggressive factor inhibition action and the protective factor potentiation action (cytoprotective effect). The toxicity test revealed that the compounds according to the present invention are very safe compounds. Thus, the antiulcer drugs containing the compounds according to the present invention are useful as preventive and curative medicines against acute and chronic gastric ulcer, duodenal ulcer, gastric hyperacidity.

The compounds (I) and their salts according to the present invention can be administered to a mammal including human as a preventive and curative medicine against acute and chronic gastric ulcers, duodenal ulcers, gastric hyperacidities. In general, it may be orally or non-orally administered in various forms of a medical composition which can be medicinally permitted.

For the oral administration, the compounds may be formed into tablets, powders and capsules together with suitable additives including excepients such as lactose, mannitols, corn starch and crystalline cellulose; binders such as a cellulose derivative, gum arabic and gelatine; disintegrators such as carboxymethyl cellulose calcium; and lubricants such as talc and magnesium stearate.

For the non-oral administration, they can be formed into injection drugs in combination with, for example, water, ethanol or glycerol.

The dosage may be determined depending upon age, symptom, effects obtained, manner of administration, and administration period. It is preferable that the dosage be once to three times a day from 1 to 500 mg/kg/day in the case of the oral administration.

EXAMPLES

The present invention will be described in details by way of examples. The present invention, however, is not limited to these examples.

EXAMPLE 1

N-[3-[3-(piperidinomethyl)phenoxy]propyl]-2-cyanoacetamide

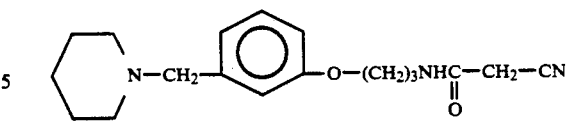

1.59 g of N-[3-[3-(piperidinomethyl)phenoxy]propyl]-2-chloroacetamide was dissolved in 9 ml of dimethylformamide in accordance with preparation method A, and 637 mg of potassium cyanide was added thereto, followed by stirring at external temperature of 90° C. for 1.5 hours. After the reaction solution was cooled down, saturated NaCl solution was added and extraction was carried out with ethyl acetate and dried over magnesium sulfate. Ethyl acetate was distilled off under reduced pressure. The thus obtained residue was dissolved in benzene, and then hydrochloric acid-ether solution was added thereto to obtain a deposited oily substance by an inclination method. Then, aqueous saturated sodium hydrogencarbonate solution was added to the thus obtained oily substance and extracted again by ethyl, dried over magnesium sulfate, distilled under reduced pressure to obtain a brown oily substance. This was subjected to silica gel column chromatography (solvent; chloroform:methanol=7:1). 418 mg of light brown oily N-[3-[3-(piperidinomethyl)phenoxy]propyl]-2-cyanoacetamide was obtained.

NMR spectrum $\delta(CDCl_3)$: 1.3 to 1.80 (6H, m) 1.80 to 2.25 (2H, m), 2.25 to 2.70 (4H,m), 3.40 (2H, s), 3.50 (2H, s), 3.20 to 3.70 (2H, m), 4.05 (2H, m), 6.60 to 7.40 (5H, m)

IR spectrum (liquid film, $cm^{-1}$): 2240, 1650

To the thus obtained N-[3-[3-(piperidinomethyl)phenoxy]propyl]-2-cyanoacetamide was added saturated maleic acid-ether solution to produce a maleic acid salt.

EXAMPLE 2

N-[3-[3-(piperidinomethyl)phenoxy]propyl]-2-(2-hydroxyethyl-1-thio)acetamide

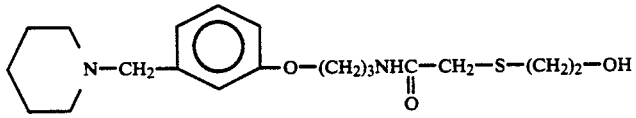

The title compound was prepared in accordance with preparation method A. 639 mg of 85% pottassium hydroxide was dissolved in 30 ml methanol, and 2.39 mg of N-[3-[3-(piperidinomethyl)phenoxy]propyl]-2-chloroacetamide and 600 mg of 2-mercaptoethanol were dropped thereto and stirred at room temperature for one hour. Then, methanol was condensed under reduced pressure. Water was added to the thus obtained residue and extracted with chloroform. The extracted solution was dried over magnesium sulfate and chloroform was distilled off under reduced pressure. Light brown oily substance was obtained.

The oily substance was then subjected to silica gel column chromatography (solvent; chloroform:methanol=4:1). As a result, 2.20 g of oily N-[3-[3-(piperidinomethyl) phenoxy]propyl]-2-(2-hydroxyethyl-1-thio)acetamide was obtained.

NMR spectrum δ(CDCl₃): 1.25 to 1.75 (6H, m), 1.85 to 2.55 (6H, m), 2.75 (2H, t), 3.27 (2H, s), 3.45 (2H, s), 3.10 to 3.95 (5H, m), 4.09 (2H, t), 6.65 to 7.60 (5H, m)

IR spectrum (liquid film, cm⁻¹): 3300, 1650

The thus obtained N-[3-[3-(piperidinomethyl)phenoxy]propyl]-2-(2-hydroxyethyl-1-thio)acetamide was converted to a hydrochloric acid salt by a hydrochloric acid-ethanol solution.

EXAMPLE 3

16.7 g of N-[3-[3-(piperidinomethyl)phenoxy]propyl]-2-(2-hydroxyethyl-1-thio)acetamide obtained in Example 2 was dissolved in 50 ml ethanol and added with a solution obtained by dissolving 11 g of 2-(4-hydroxybenzoyl)-benzoic acid (hybenzoic acid) in 70 ml ethanol, and stirred. The reaction solution was substantially halved by condensation and then allowed to stand at 5° C. for 24 hours. Crystals precipitated were collected by filtration and 25 g (90%) of N-[3-[3-(piperidinomethyl)phenoxy]propyl]-2-(2-hydroxyethyl-1-thio)acetamide hybenzoic acid salt was obtained.

Melting point: 145° to 148° C.

NMR δ(DMSO): 1.33 to 1.53 (6H, br), 1.84 (2H, m), 2.42 to 2.56 (4H, br), 2.63 (2H, m), 3.11 (2H, s), 3.21 (2H, q), 3.54 (2H, t), 3.58 (2H, s), 3.95 (2H, t), 6.78 to 7.96 (12H, m), 8.09 (1H, br)

IR (KBr) cm⁻¹: 3350, 2950, 1640, 1580, 1390, 1290, 1150, 930, 845, 760

EXAMPLE 4

14.4 g of N-[3-[3-(piperidinomethyl)phenoxy]propyl]-2-(2-hydroxyethyl-1-thio)acetamide prepared in Example 2 was dissolved in 50 ml benzene, and 200 ml ether solution containing 4.55 g maleic acid was added thereto. The supernatant was removed by inclination, and the residue was washed with 200 ml ether followed by drying-up under reduced pressure. 13.8 g of oily maleic acid salt was obtained.

NMR δ(CDCl₃): 1.24 (1H, br), 1.85 to 1.98 (5H, m), 2.05 (2H, m), 2.54 to 2.68 (2H, br), 3.76 (2H, t), 3.29 (2H, s), 3.48 (2H, q), 3.46 to 3.60 (2H, m), 3.79 (2H, t), 4.02 (2H, t), 4.11 (2H, s), 6.34 (2H, s), 6.84 to 7.32 (4H, m), 7.50 (1H, s)

IR (liquid film, cm⁻¹): 3300, 1640, 1580, 1340, 1260, 860

EXAMPLE 5

15 g of γ-cyclodextrin was dissolved in 60 ml water. 2.1 g of N-[3-[3-(piperidinomethyl)phenoxy]propyl]-2-(2-hydroxyethyl-1-thio)acetamide obtained in Example 2 was added thereto and subjected to ultrasonic treatment for 15 minutes. Then, it was stirred at room temperature for 20 hours. Crystals were collected by filtration, washed twice with 10 ml water, recrystalized from water, dried up at 60° C. for 6 hours to obtain 13.6 g of γ-cyclodextrin inclusion compound of N-[3-[3-(piperidinomethyl)phenoxy]propyl]-2-(2-hydroxyethyl-1-thio)acetamide.

Melting point: about 275° C. (dec.)
IR: 1640 cm⁻¹

EXAMPLE 6

N-[3-[3-(piperidinomethyl)phenoxy]propyl]-2-(2-hydroxyethyl-1-sulfinyl)acetamide

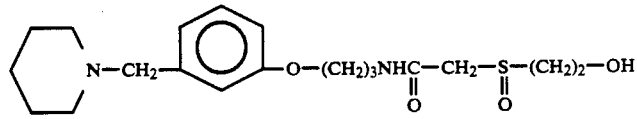

The title compound was prepared according to preparation method E. 1.23 g of N-[3-[3-(piperidinomethyl)phenoxy]propyl]-2-(2-hydroxyethyl-1-thio)acetamide prepared in Example 2 and 738 mg of aqueous hydrogen peroxide solution were added to 3 ml acetic acid. The solution was stirred at room temperature for 1.5 hours and was made alkaline with saturated aqueous sodium bicarbonate solution, which was extracted with chloroform. The extracted solution was dried over potassium carbonate, and then chloroform was distilled off under reduced pressure. Oily substance was obtained. The obtained substance was then subjected to silica gel column chromatography (solvent; chloroform:methanol=3:1). As a result, 512 mg of oily N-[3-[3-(piperidinomethyl)phenoxy]propyl]-2-(2-hydroxyethyl-1-sulfinyl)acetamide was obtained.

NMR spectrum δ(CDCl₃): 1.32 to 1.84 (6H, m), 1.88 to 2.18 (2H, m), 2.31 to 2.71 (4H, m), 2.88 to 4.28 (12H, m), 6.66 to 7.42 (4H, m), 7.53 to 7.96 (1H, br)

IR spectrum (liquid film, cm⁻¹): 1655, 1260, 1035

EXAMPLE 7

N-[3-[3-(piperidinomethyl)phenoxy]propyl]-2-(2-hydroxyethylsulfonyl)acetamide

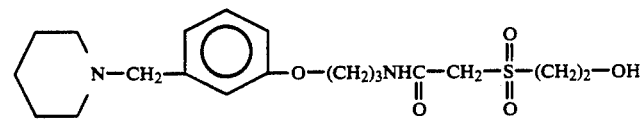

The title compound was prepared according to preparation method E. 1.30 g of N-[3-[3-(piperidinomethyl)phenoxy]propyl]-2-(2-hydroxyethyl-1-thio)acetamide prepared in Example 2 was dissolved in 8 ml acetic acid, to which 8.34 g of aqueous 30% hydrogen peroxide solution was added. It was then stirred at external temperature of 70° C. for 1.5 hours. 10 ml water was added to the reaction solution and condensed under reduced pressure. The obtained residue liquid was neutralized with saturated aqueous sodium hydrogencarbonate solution and then NaCl was added to make an aqueous saturated solution, which was extrated with chloroform. The chloroform layer was dried over magnesium sulfate, and chloroform was distilled off under reduced pressure. Oily substance was obtained. The thus obtained oily substance was then subjected to silica gel column chromatography (solvent; chloroform:methanol=4:1). As a result, 572 mg of light yellow oily N-[3-[3-(piperidinomethyl)phenoxy]propyl]-2-(2- hydroxyethyl-1-sulfonyl)acetamide containing a slight quantity of acetic acid was obtained.

NMR spectrum δ(CDCl₃): 1.35 to 2.30 (8H, m), 2.35 to 2.95 (4H, m), 3.10 to 4.45 (13H, m), 6.60 to 7.50 (4H, m), 7.70 to 8.25 (1H, m)

IR spectrum (liquid film, cm⁻¹): 3300, 1315, 1120

The thus obtained N-[3-[3-(piperidinomethyl)phenoxy]propyl]-2-(2-hydroxyethylsulfonyl)acetamide was convered to a hydrochloric acid salt with hydrochloric acid-ethanol solution.

EXAMPLE 8

N-[3-[3-(1-pyrrolidinylmethyl)phenoxy]propyl]-2-(2-hydroxyethyl-1-thio)acetamide

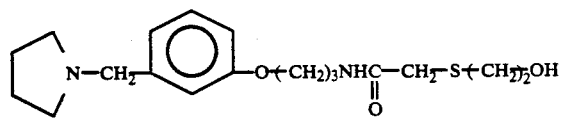

Preparation method A was followed. 361 mg of 85% potassium hydroxide was dissolved in 35 ml methanol, to which 1.13 g of N-[3-[3-(1-pyrrolidinylmethyl)phenoxy]propyl]-2-chloroacetamide and 324 mg of 2-mercaptoethanol were added and stirred at room temperature for 2 hours. Methanol was then condensed under reduced pressure. Then, 30 ml water was added to the thus obtained residue, and the extracted solution extracted with chloroform was dried over magnesium sulfate. Chloroform was distilled off under reduced pressure. Light brown oily substance was obtained.

This substance was subjected to silica gel column chromatography (solvent; chloroform:methanol=4:1). 836 mg of oily N-[3-[3-(1-pyrrolidinylmethyl)phenoxy]propyl]-2-(2-hydroxyethyl-1-thio)acetamide was obtained.

NMR spectrum δ(CDCl₃): 1.70 to 2.35 (6H, m) 2.35 to 2.90 (6H, m), 3.15 to 4.36 (11H, m), 6.65 to 7.63 (5H, m)

IR spectrum (liquid film, cm⁻¹): 3300, 1650

EXAMPLE 9

N-[3-[3-(1-pyrrolidinylmethyl)phenoxy]propyl]-2-(2-hydroxyethyl-1-sulfinyl)acetamide

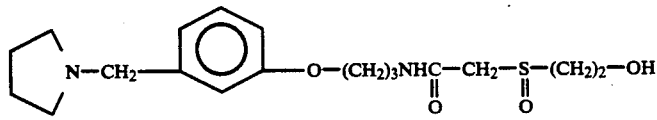

Preparation method E was followed. 918 mg of N-[3-[3-(1-pyrrolidinylmethyl)phenoxy]propyl]-2-(2-hydroxyethyl-1-thio)acetamide obtained in Example 8 was dissolved in 3 ml acetic acid, to which 549 mg of aqueous 31% hydrogen peroxide solution was dropped at room temperature. Stirring was continued at the same temperature. After 1.5 hours, it was then added into saturated aqueous sodium hydrogencarbonate solution, made saturated by sodium chloride and extracted by n-butanol. The extracted solution was dried over magnesium sulfate and n-butanol was distilled off under reduced pressure. 804 mg of light brown oily substance was obtained. The thus obtained substance was then subjected to alumina column chromatography (Melck Co., Art 1067, solvent; chloroform:methanol=7:1).

671 mg of oily N-[3-[3-(1-(pyrrolidinylmethyl)-phenoxy]propyl]-2-(2-hydroxyethyl-1-sulfinyl)acetamide was obtained.

NMR spectrum δ(CDCl₃): 1.60 to 2.20 (6H, m), 2.30 to 2.75 (4H, m), 3.03 (2H, t), 3.20 to 4.25 (11H, m), 6.65 to 7.65 (5H, m)

IR spectrum (liquid film, cm⁻¹): 3275, 1650, 1025

EXAMPLE 10

N-[3-[3-(1-(pyrrolidinylmethyl)phenoxy]propyl]-2-(2-hydroxyethyl-1-sulfonyl)acetamide

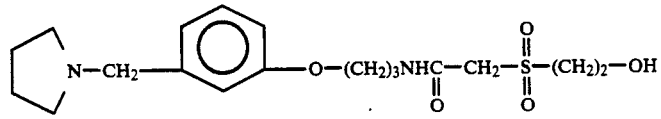

Preparation method E was followed. 1.27 g of N-[3-[3-(1-(pyrrolidinylmethyl)phenoxy]propyl]-2-(2-hydroxyethyl-1-thio)acetamide obtained in Example 8 was dissolved in 8 ml acetic acid, to which 9.11 g of aqueous 31% hydrogen peroxide solution was added and stirred at external temperature of 65° C. 1.5 hours after, 10 ml water was added and condensed under reduced pressure. The residual solution was added with 16 ml of saturated aqueous sodium hydrogencarbonate solution and extracted with chloroform. The extracted solution was dried over magnesium sulfate, and then chloroform was distilled off under reduced pressure to obtain a brown oily substance. This was then subjected to siliga gel column chromatography (solvent; chloroform:methanol=4:1). As a result, 377 mg of colorless oily N-[3-[3-(1-pyrrolidinylmethyl)phenoxy]propyl]-2-(2-hydroxyethyl-1-sulfonyl)acetamide containing a slight quantity of acetic acid was obtained.

NMR spectrum δ(CDCl₃): 1.75 to 2.30 (6H, m), 2.65 to 3.25 (4H, m), 3.25 to 3.70 (m), 3.80 to 4.50 (m), 6.65 to 7.75 (5H, m)

IR spectrum (liquid film; cm⁻¹): 3300, 1650, 1310, 1115

EXAMPLE 11

N-[3-[3-(1-piperidinomethyl)phenoxy]propyl]-2-(2-acetoxyethylsulfonyl)acetamide

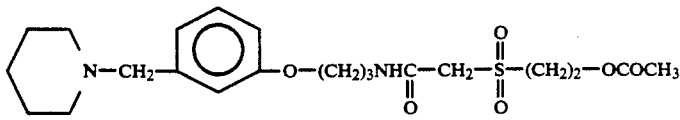

897 mg of N-[3-[3-(piperidinomethyl)phenoxy]-propyl]-2-(2-hydroxyethylsulfonyl)acetamide obtained in Example 7 was dissolved in 428 mg of acetic anhydride and 462 mg of pyridine and stirred at external temperature of 55° C. for 2 hours. Then, it was added to a mixture of 20 ml saturated aqueous NaCl solution and 15 ml saturated aqueous sodium hydrogencarbonate solution and was extracted with chloroform. The extracted solution was dried over magnesium sulfate, and then chloroform was distilled off under reduced pressure to obtain an oily substance. The thus obtained substance was subjected to silica gel column chromatography (solvent; chloroform:methanol=4:1). As a result, 583 mg of light brown oily N-[3-[3-(piperidinomethyl)phenoxy]propyl]-2-(2-acetoxyethyl-sulfonyl)acetamide containing a slight quantity of acetic acid was obtained.

NMR spectrum δ(CDCl₃): 1.40 to 2.20 (5H, m), 2.10 (3H, s), 2.60 to 3.05 (4H, m), 3.05 to 4.70 (12H, m), 6.60 to 7.70 (4H, m), 8.05 to 8.40 (1H, m)

IR spectrum (liquid film, cm⁻¹): 1740, 1665, 1320, 1120

The thus obtained N-[3-[3-(piperidinomethyl)phenoxy]propyl]-2-(2-acetoxyethylsulfonyl)acetamide was converted to a maleic acid salt by a saturated ether solution of maleic acid.

NMR spectrum δ(CDCl₃): 1.60 to 2.30 (6H, m), 2.05 (3H, s), 2.30 to 3.05 (6H, m), 3.20 to 3.85 (6H, m), 3.95 to 4.50 (4H, m), 6.35 (2H, s), 6.70 to 7.60 (5H, m).

IR spectrum (liquid film, cm⁻¹): 1735, 1640

EXAMPLE 12

N-[3-[3-(1-pirrolidinylmethyl)phenoxy]propyl]-2-(2-acetoxyethyl-1-thio)acetamide dried over magnesium sulfate, and then chloroform was distilled off under reduced pressure. The obtained residue was subjected to silica gel column chromatography (solvent; chloroform:methanol=4:1). As a result, 318 mg of oily N-[3-[3-(1-pyrrolidinylmethyl)phenoxy]-propyl]-2-(2-acetoxyethyl-1-thio)acetamide was obtained.

NMR spectrum δ(CDCl₃): 1.60 to 2.30 (6H, m), 2.05 (3H, s), 2.30 to 3.10 (6H, m), 3.10 to to 3.85 (6H, m) 3.95 to 4.40 (4H, m), 6.70 to 7.60 (5H, m)

IR spectrum (liquid film, cm⁻¹): 1735, 1645

The thus obtained N-[3-[3-(1-pyrrolidinylmethyl)-phenoxy]propyl]-2-(2-acetoxyethyl-1-thio)acetamide was converted into a maleic acid salt with a saturated ether solution of maleic acid.

EXAMPLE 13

N-[3-[3-(piperidinomethyl)phenoxy]propyl]-2-(2-acetoxyethyl-1-thio)acetamide

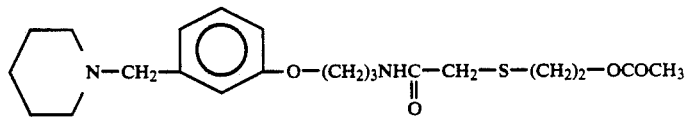

1.03 g of N-[3-[3-(piperidinomethyl)phenoxy]propyl]-2-(2-hydroxyethyl-1-thio)acetamide obtained in Example 2 was dissolved in a mixture of 1.19 g of acetic anhydride and 981 mg of pyridine and stirred at external temperature of 60° C. for 2 hours. Then, 10 ml water and 10 ml saturated aqueous sodium hydrogencarbonate solution were added and extracted with chloroform. The extracted solution was dried over magnesium sulfate, and then chloroform was distilled off under reduced pressure. The obtained residue was subjected to silica gel column chromatography (solvent; chloroform:methanol=4:1). As a result, 637 mg of oily N-[3-[3-(piperidinomethyl)phenoxy]propyl]-2-(2-acetoxyethyl-1-thio)acetamide was obtained.

NMR spectrum δ(CDCl₃): 1.25 to 1.78 (6H, m), 1.78

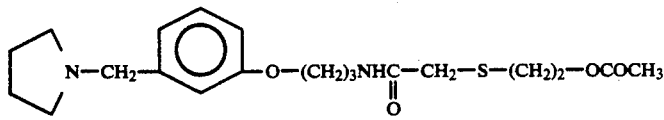

404 mg of N-[3-[3-(1-pyrrolidinyl)phenoxy]propyl]-2-(2-hydroxyethyl-1-thio)acetamide obtained in Example 8 was dissolved in a mixture of 261 mg acetic anhydride and 250 mg pyridine and stirred at external temperature of 55° C. for 30 minutes. Then, 20 ml of saturated aqueous NaCl solution and 15 ml saturated aqueous sodium hydrogencarbonate solution were added thereto and extracted with chloroform. The extracted solution was to 2.56 (6H, m), 2.01 (3H, s), 2.78 (2H, t), 3.22 (2H, s), 3.20 to 3.72 (4H, m), 3.78 to 4.42 (4H, m), 6.51 to 7.61 (5H, m)

IR spectrum (liquid film, cm⁻¹): 1745, 1650

EXAMPLE 14

N-[3-[3-(piperidinomethyl)phenoxy]propyl]-2-(2,3-dihydroxypropyl-1-thio)acetamide

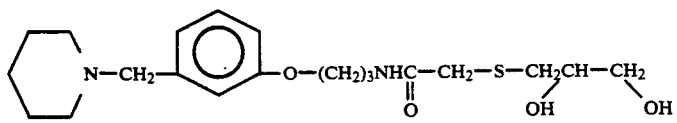

Preparation method A was followed. 375 mg of 85% potassium hydroxide was dissolved in 20 ml methanol, to which were added at once 5 ml methanol solution of 399 mg 3-mercapto-1,2-propanediol and 5 ml methanol solution of 1.20 g N-[3-[3-(piperidinomethyl)phenoxy]-propyl]-2-chloroacetamide. The reaction solution was stirred at room temperature for one hour, and methanol was condensed under reduced pressure. 60 ml saturated aqueous NaCl solution was added to the obtained residue and extracted with chloroform. The extracted solution was dried over magnesium sulfate, and then chloroform was distilled off under reduced pressure to obtain a light brown oily substance. The thus obtained substance was subjected to silica gel column chromatography (solvent; chloroform: methanol=4:1). As a result, 828 mg of colorless oily N-[3-[3-(piperidinomethyl)-phenoxy]propyl]-2-(2,3-dihydroxypropyl-1-thio)acetamide was obtained.

NMR spectrum δ(CDCl₃): 1.39 to 1.80 (6H, m), 1.80 to 2.22 (2H, m), 2.30 to 2.70 (4H, m), 2.74 (2H, d), 3.26 (2H, s), 3.50 (2H, s), 3.32 to 3.82 (7H, m), 4.10 (2H, t), 6.65 to 7.80 (5H, m)

IR spectrum (liquid film, cm⁻¹): 3350, 1630

The thus obtained N-[3-[3-(piperidinomethyl) phenoxy]propyl]-2-(2,3-dihydroxypropyl-1-thio)acetamide was converted into a hydrochloric acid salt with hydrochloric acid-ethanol solution.

EXAMPLE 15

N-[3-[3-(piperidinomethyl)phenoxy]propyl]-2-[(2,2-dimethyl-1,3-dioxolan-4-yl)methylthio]acetamide distilled off under reduced pressure. The obtained light brown oily substance was subjected to silica gel column chromatography (solvent; chloroform:methanol=5:1). 594 mg of oily N-[3-[3-(piperidinomethyl)phenoxy]-propyl]-2-[(2,2-dimethyl-1,3-dioxolan-4-yl)methylthio]acetamide was obtained.

NMR spectrum δ(CDCl₃): 1.33 (3H, s), 1.41 (3H, s), 1.30 to 1.80 (6H, m), 1.80 to 2.25 (2H, m), 2.25 to 2.60 (4H, m), 2.71 (2H, d), 3.30 (2H, s), 3.45 (2H, s), 3.40 to 3.85 (2H, m), 3.85 to 4.45 (5H, m), 6.60 to 7.50 (5H, m)

IR spectrum (liquid film, cm⁻¹): 1645

EXAMPLE 16

N-[3-[3-(piperidinomethyl)phenoxy]propyl]-2-(ethoxycarbonylmethylthio)acetamide

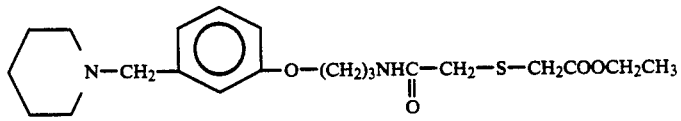

Preparation method A was followed. 778 mg of 85% potassium hydroxide was dissolved in 50 ml ethanol. Then, 10 ml ethanol solution of 3.00 g of N-[3-[3-(piperidinomethyl)phenoxy]propyl]-2-chloroacetamide and 1.14 g of 2-mercapto ethyl acetate were added to this solution. It was stirred at room temperature for 30 minutes, and ethanol was condensed under reduced pressure. Then, water was added to the obtained residue and extracted with chloroform. The extracted solution was dried over magnesium sulfate, and chloroform was distilled off under reduced pressure. Light brown oily substance was obtained. The thus obtained substance was subjected to silica gel column chromatography (solvent; ethyl acetate). As a result, 2.22 g of N-[3-[3-(piperidinomethyl)phenoxy]propyl]-2-(ethoxycarbonylmethylthio)acetamide was obtained.

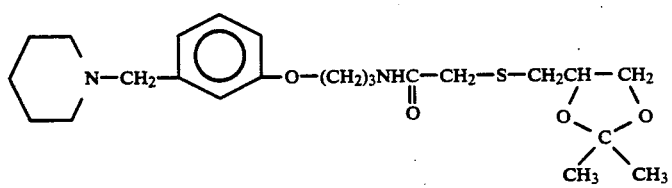

50 ml acetone and 5 ml of 7% hydrochloric acid-ethanol solution were added to 2.10 g of N-[3-[3-(piperidinomethyl) phenoxy]propyl]-2-(2,3-dihydroxypropyl-1-thio)acetamide prepared in Example 14 and refluxed over 2 hours. Then, the solvent was distilled off under reduced the pressure. 10 ml saturated aqueous NaCl solution and 10 ml saturated aqueous sodium hydrocarbonate solution were added to the residue and extracted with ethyl acetate. The extracted solution was dried over magnesium sulfate, and then the solvent was NMR spectrum δ(CDCl₃): 1.25 (3H, t), 1.30 to 1.75 (6H, m), 1.85 to 2.20 (2H, m), 2.20 to 2.60 (4H, m), 3.27 (2H, s), 3.35 (2H, s), 3.44 (2H, s), 3.57 (2H, t), 4.06 (2H, t), 4.11 (2H, t), 6.70 to 7.50 (5H, m)

IR spectrum (liquid film, cm⁻¹): 1730, 1650

Melting point: 137° to 137.5° C.

EXAMPLE 17

N-[3-[3-(piperidinomethyl)phenoxy]propyl]-2-(ethoxycarbonylmethylsulfonyl)acetamide

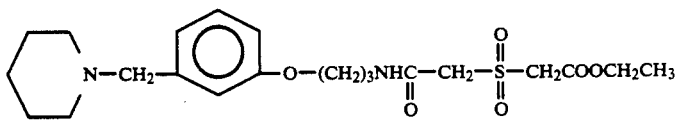

Preparation method E was followed. 2.13 g of N-[3-[3-(piperidinomethyl)phenoxy]propyl]-2-(ethoxycarbonylmethylthio)acetamide obtained in Example 16 was dissolved in 20 ml acetic acid, to which 20 ml of aqueous 30% hydrogen peroxide solution was added and stirred at external temperature of 70° C. for 2 hours. Then, water was added to the reaction solution and condensed under reduced pressure. The obtained residual liquid was neutralized with saturated sodium hydrogencarbonate and was added with NaCl to make a saturated aqueous solution, followed by extraction with chloroform. The extracted solution was dried over magnesium sulfate, and then chloroform was distilled off under reduced pressure. The obtained residue was subjected to silica gel column chromatography (solvent; chloroform:methanol=4:1). 1.34 g of oily N-[3-[3-(piperidinomethyl)phenoxy]propyl]-2-(ethoxycarbonylmethylsulfonyl)acetamide containing a slight quantity of acetic acid was obtained.

NMR spectrum δ(CDCl$_3$): 1.30 (3H, t), 1.40 to 2.25 (8H, m), 2.35 to 2.80 (4H, m), 3.17 (2H, s), 3.56 (2H, t), 4.35 (4H, brs), 3.95 to 4.55 (4H, m), 6.70 to 7.70 (5H, m)

IR spectrum (liquid film, cm$^{-1}$): 1740, 1675, 1335, 1120

The thus obtained N-[3-[3-(piperidinomethyl)phenoxy]propyl]-2-(ethoxycarbonylmethylsulfonyl)acetamide was converted into a hydrochloric acid salt with hydrochloric acid-ethanol solution.

EXAMPLE 18

N-[3-[3-(piperidinomethyl)phenoxy]propyl]-2-carbamoylacetamide

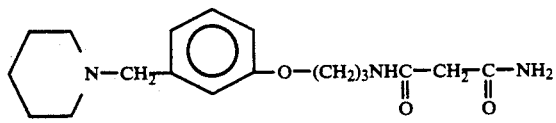

Preparation method D was followed. 1.37 g of N-[3-[3-(piperidinomethyl)phenoxy]propyl]-2-methoxycarbonylacetamide prepared in Example 22 to be described later was dissolved in 30 ml of 9.3% (w/v) ammonia-methanol solution and heated at 50° C. for 8 hours in a sealed tube. Then, methanol was distilled off under reduced pressure. The obtained residue was subjected to silica gel column chromatography (solvent; chloroform: methanol=4:1). 669 mg of N-[3-[3-(piperidinomethyl)phenoxy]propyl]-2-carbamoylacetamide was obtained as colorless crystals.

Melting point: 85.3° to 88.3° C.

NMR spectrum δ (CDCl$_3$): 1.35 to 1.80 (6H, m), 1.80 to 2.10 (2H, m), 2.20 to 2.65 (4H, m), 3.20 (2H, s), 3.45 (2H, s), 3.55 (2H, t), 4.05 (2H, t), 5.50 to 6.10 (2H, brs), 6.60 to 7.50 (5H, m)

IR spectrum (liquid film, cm$^{-1}$): 3300, 1650

The thus obtained N-[3-[3-(piperidinomethyl)phenoxy]propyl]-2-carbamoylacetamide was converted into a hydrochloric acid salt with hydrochloric acid-ethanol solution.

Melting point: 195.5° to 197.5° C.

EXAMPLE 19

N-[3-[3-(pyrrolidinylmetyl)phenoxy]propyl]-2-carbamoylacetamide

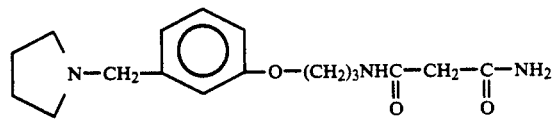

Preparation method D was followed. 1.30 g of N-[3-[3-(1-pyrrolidinylmethl)phenoxy]propyl]-2-methoxycarbonylacetamide prepared in Example 23 to be described later was dissolved in 30 ml of 9.3% ammonia-methanol solution and stirred at room temperature for 14 hours in a sealed tube. Then, methanol was distilled off under reduced pressure. The obtained residue was subjected to silica gel column chromatography (solvent; chloroform: methanol=6:1). 950 mg of oily N-[3-[3-(pyrrolidinylmethl)phenoxy]propyl]-2-carbamoylacetamide was obtained.

NMR spectrum δ(CDCl$_3$): 1.59 to 2.20 (6H, m), 2.37 to 2.79 (4H, m), 3.13 to 3.79 (6H, m), 4.02 (2H, t), 6.26 to 7.92 (6H, m).

IR spectrum (liquid film, cm$^{-1}$): 2950, 1670, 1640

The thus obtained N-[3-[3-(pyrrolidinylmethl)phenoxy]propyl]-2-carbamoylacetamide was converted into a hydrochloric acid salt with hydrochloric acid-ethanol solution.

EXAMPLE 20

N-[3-[3-(piperidinomethyl)phenoxy]propyl]-2-[N',N'-[di(2-hydroxyethyl)]carbomoyl]acetamide

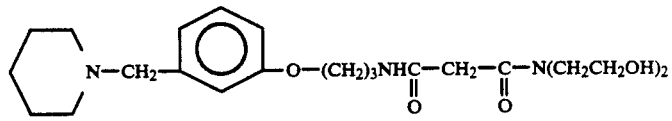

Preparation method D was followed. 777 mg of diethanolamine was added to 1.58 g of N-[3-[3-(piperidinomethyl)phenoxy]propyl]-2-methoxycarbonylacetamide prepared in Example 22 to be described later and stirred at external temperature of 110° C. for 3 hours. The reaction solution was subjected to silica gel column chromatography (solvent; chloroform: methanol=4:1). 913 mg of light brown oily N-[3-[3-(piperidinomethyl)phenoxy]propyl]-2-[N',N'-[di(2-hydroxyethyl)]carbomoyl]acetamide was obtained.

NMR spectrum δ (CDCl₃): 1.30 to 1.75 (6H, m), 1.80 to 2.15 (2H, m), 2.20 to 2.65 (4H, m), 3.47 (2H, m), 3.35 to 4.80 (16H, m), 6.60 to 7.50 (4H, m), 7.82 (1H, brs)

IR spectrum (liquid film, cm⁻¹): 3300, 1645, 1625,

The thus obtained N-[3-[3-(piperidinomethyl)phenoxy]propyl]-2-[N',N'-[di(2-hydroxyethyl)]carbomoyl]acetamide was converted into a hydrochloric acid salt with hydrochloric acid-ethanol solution.

EXAMPLE 21

N-[3-[3-(piperidinomethyl)phenoxy]propyl]-3-oxobutylamide

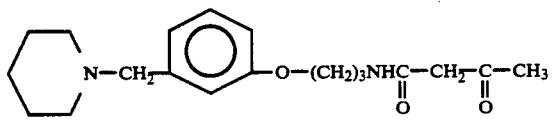

Preparation method B was followed. 1.34 g of 3-[3-(piperidinomethyl)phenoxy]propylamine was dissolved in 10 ml methylene chloride, to which 527 mg of diketene was dropped.

Ten minutes after completion of the dropping, methylene chloride was distilled off under reduced pressure. The obtained residue was subjected to silica gel column chromatography (solvent; chloroform:methanol=5:1). 1.27 g of colorless oily N-[3-[3-(piperidinomethyl)phenoxy]propyl]-3-oxobutylamide was obtained.

NMR spectrum δ (CDCl₃): 1.30 to 1.80 (6H, m), 1.80 to 2.60 (6H, m), 2.25 (3H, s), 3.25 to 3.75 (6H, m), 4.05 (2H, t), 6.60 to 7.55 (5H, m)

IR spectrum (liquid film, cm⁻¹): 1720, 1645

The thus obtained N-[3-[3-(piperidinomethyl)phenoxy]propyl]-3-oxobutylamide was converted to hydrochloric acid salt with hydrochloric acid - ethanol solution.

EXAMPLE 22

N-[3-[3-(piperidinomethyl)phenoxy]propyl]-2-methoxycarbonylacetamide

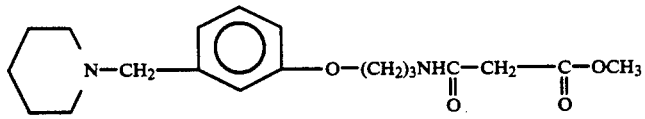

Preparation method B was followed.

2.47 g of [3-[3-(piperidinomethyl)phenoxy]propylamine was dissolved n 40 ml of dimethylmalonate and stirred at external temperature of 130° C. for 2 hours. Then, an excessive quantity of dimethylmalonate was distilled of under reduced pressure. Light brown oily substance was obtained. The obtained substance was subjected to silica gel column chromatography (solvent; chloroform:methanol=6:1). As a result, 3.06 g of oily N-[3-[3-(piperidinomethyl)phenoxy]propyl]-2-methoxycarbonylacetamide was obtained.

NMR spectrum δ (CDCl₃): 1.30 to 2.15 (12H, m), 3.40 (2H, s), 3.51 (2H, s), 3.80 (3H, s), 3.20 to 4.30 (4H, s), 6.60 to 7.70 (5H, m)

IR spectrum (liquid film, cm⁻¹): 1735, 1645

The thus obtained N-[3-[3-(piperidinomethyl)phenoxy]propyl]-2-methoxycarbonylacetamide was converted to a maleic acid salt with saturated ether solution of maleic acid.

EXAMPLE 23

N-[3-[3-(1-pyrrolidinylmethyl)phenoxy]propyl]-2-methoxycarbonylacetamide

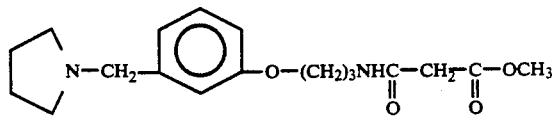

Preparation method B was followed. 2.00 g of 3-[3-(1-pyrrolidinylmethyl)phenoxy]propylamine was dissolved in 40 ml of dimethylmalonate and stirred in an oil bath at 130° C. over 3 hours, followed by condensation under reduced pressure. The obtained residue was subjected to silica gel column chromatography (solvent; ethyl acetate). 2.50 g of oily N-[3-[3-(1-pyrrolidinylmethyl)phenoxy]propyl]-2-methoxycarbonylacetamide was obtained.

NMR spectrum δ (CDCl₃): 1.57 to 2.18 (6H, m), 2.36 to 2.78 (4H, m), 3.18 to 3.79 (7H, m), 4.06 (2H, t), 3.66 to 7.75 (4H, m)

IR spectrum (liquid film, cm⁻¹): 2950, 1740, 1650

EXAMPLE 24

N-[3-[3-(piperidinomethyl)phenoxy]propyl]-2-sulfamoylacetamide

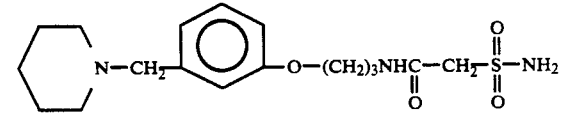

Preparation method B was followed. 1.36 g of N-[3-[3-(piperidinomethyl)phenoxy]propylamine and 1.15 g of 2-sulfamoylethylacetate were mixed and stirred at external temperature of 130° C. over 4 hours. It is then subjected to silica gel column chromatography (solvent; chloroform:methanol=4:1). 1.34 g of oily N-[3-[3-(1-piperidinomethyl)phenoxy]propyl]-2-sulfamoylacetamide was obtained.

IR spectrum (liquid film, cm⁻¹): 1655, 1440, 1155

EXAMPLE 25

N-[3-[3-(piperidinomethyl)phenoxy]propyl]-2-(2,5-dimethylimidazol-4-yl-methylthio)acetamide

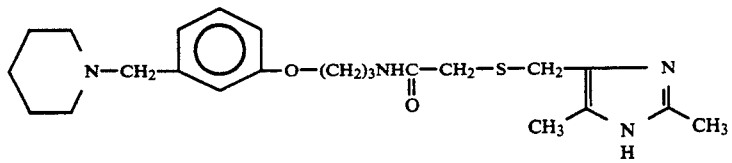

Preparation method B was followed. 2.68 g of [3-[3-(piperidinomethyl)phenoxy]propylamine was added to 2.33 g of 4-[(ethoxy carbonyl methyl)thio]methyl-2,5-dimethylimidazol and stirred in an oil bath of 110° C. for 6 hours. The obtained oily substance was subjected to silica gel column chromatography (solvent; chloroform: methanol=7:1). 1.43 g of N-[3-[3-(piperidinomethyl)phenoxy]propyl]-2-(2,5-dimethylimidazol-4-yl-methylthio)acetamide was obtained.

NMR spectrum δ (CDCl₃): 1.37 to 1.73 (6H, m), 1.88 to 2.59 (12H, m), 3.08 to 4.28 (10H, m), 6.63 to 7.43 (4H, m)

IR spectrum (liquid film, cm⁻¹): 2930, 1650, 1445, 1260

The thus obtained N-[3-[3-(piperidinomethyl)phenoxy]propyl]-2-(2,5-dimethylimidazol-4-yl-methylthio)acetamide was converted to a hydrochloric acid salt with hydrochloric acid-ethanol solution.

EXAMPLE 26

The compound of Example 2 was prepared in accordance with preparation method C.

2.50 g of [3-[3-(piperidinomethyl)phenoxy]phenoxy]-propylamine dissolved in 10 ml benzene was dropped into a solution of 20 ml benzene and 1.20 g of 1.4-thioxane-2-on under stirring at room temperature for one hour. Saturated ether solution of maleic acid was added to the reaction solution until precipitation was completed. Then, it was cooled down, and the supernatant was removed. 50 ml of chloroform was added to the residue and washed with saturated sodium carbonate solution. Furthermore, it was washed with 30 ml chloroform, and the chloroform was combined again, followed by drying over sodium sulfate anhydride. Thereafter, chloroform was distilled off under reduced pressure. 3.41 g of oily N-[3-[3-(piperidinomethyl)phenoxy]-propyl-2-(2-hydroxy-1-thio)acetamide was obtained.

EXAMPLE 27

The compound of Example 2 was prepared in accordance with preparation method B.

2.03 g of 2-(2-hydroxyethyl-1-thio)ethylacetate was added to a 20 ml benzene solution containing 2.84 g of [3-[3-(piperidinomethyl)phenoxy]propylamine under stirring at room temperature. Stirring was carried out for further 30 minutes. Then, it was refluxed at 70° C. over one hour. After cooling down, a saturated ether solution of maleic acid was added to the reaction solution until no precipitation was deposited. The supernatant was removed. The residue was dissolved with 50 ml of chloroform, washed with saturated aqueous sodium hydrogencarbonate solution. Furthermore, the aqueous layer was extracted with 30 ml of chloroform, and the chloroform was combined again and dried over sodium sulfate anhydride. Chloroform was distilled off under reduced pressure. 2.50 g of oily N-[3-[3-(piperidinomethyl)phenoxy]propyl-2-(2-hydroxyethyl-1-thio)acetamide was obtained.

| Medicine Preparation Example 1. | |
|---|---|
| Compound of Example 2 | 20 g |
| Lactose | 315 g |
| Corn Starch | 125 g |
| Crystalline Cellulose | 25 g |

The above ingredients were uniformly mixed, to which 200 ml of aqueous 7.5% hydroxypropyl cellulose solution was added, followed by forming it into granules by an extrusion granulating machine with a 0.5 mm-diameter screen. The granules were immediately rounded by a rounding machine and dried.

| Medicine Preparation Example 2 | |
|---|---|
| Compound of Example 3 | 20 g |
| Lactose | 100 g |
| Corn Starch | 36 g |
| Crystalline Cellulose | 30 g |
| Carboxymethylcellulose Calcium | 10 g |
| Magnesium stearate | 4 g |

The above ingredients were uniformly mixed, and were formed into tablets each weighing 200 mg on a single tablet-forming machine having a stamp whose diameter was 7.5 mm.

| Medicine Preparation Example 3 | |
|---|---|
| Compound of Example 7 | 40 g |
| Lactose | 232 g |
| Corn Starch | 108 g |
| Polyvinyl Pyrrolidone | 20 g |

The above ingredients were uniformly mixed, to which 180 ml of 70 (v/v) % isopropylalcohol was added. It was then formed into granules by an extrusion granulating machine with a 0.5 mm-diameter screen, and dried. The thus formed granules were encapsulated in #2 hard gelatinous capsules, each contained 240 mg granules.

| Medicine Preparation Example 4 | |
|---|---|
| Compound of Example 8 | 3 g |
| Polysolvate 80 | 20 g |

The above ingredients and 8 g of NaCl were dissolved in distilled water to make the total quantity 1000 ml. This solution was filtered, sterilized and charged in ampoules with a content of 1 ml under sterilized conditions to prepare an injection drug.

INDUSTRIAL APPLICABILITY

The compounds (I), salts thereof and their cyclodextrin inclusion compounds according to this invention are safe compounds having both aggressive factor inhibiting action and protective factor potentiation action (cytoprotective effect). Antiulcer drugs containing them are useful as preventive and curative medicines against both acute and chronic gastric ulcers, duodenal ulcers and gastric hyperacidities.

What is claimed is:

1. A compound of the formula (I):

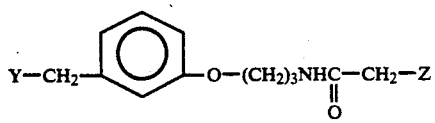

in which Y is piperidino, 1-pyrrolidinyl, or 3-hydroxy-1-pyrrolidinyl, and Z is a group selected from the group consisting of those having the formulas (a) to (e):

(a) cyano;

(b) a group of the formula

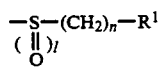

in which $l$ represents an integer from 0 to 2, n represents an integer from 1 to 3, $R^1$ is a hydroxy group, 1,2-dihydroxyethyl group, 1-hydroxyethyl group, 2-phenoxy-1-hydroxyethyl group, 2-hydroxyethoxy group, lower alkoxycarbonyl group, 2,2-dimethyl-1,3-dioxolan-4-yl group, or a lower acyloxymethyl group;

(c) a group of the formula

in which $R^2$ is amino, lower alkylamino, di(2-hydroxyethyl)amino, lower alkyl, or lower alkoxy;

(d) a group of the formula

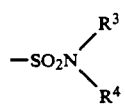

in which $R^3$ and $R^4$ independently are hydrogen or lower alkyl; and (e) a group of the formula

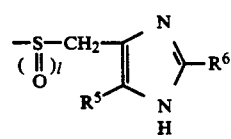

in which $l$ represents an integer from 0 to 2, and $R^5$ and $R^6$ independently are hydrogen or lower alkyl;

or a salt or cyclodextrin inclusion compound thereof.

2. An inclusion compound which is obtained by including a compound of claim 1 in cyclodextrin.

3. An antiulcer composition comprising a pharmaceutically acceptable carrier, and as an active ingredient, a therapeutically effective amount of the substituted acetamide derivative or a salt thereof or a cyclodextrin inclusion compound thereof as described in claim 1.

4. A compound of claim 1, wherein Z is cyano.

5. A compound of claim 1, wherein Z is

in which $R^2$ is amino, lower alkylamino, di(2-hydroxyethyl)amino, lower alkyl, or lower alkoxy.

6. A compound of claim 1, wherein Z is

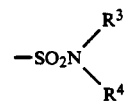

in which $R^3$ and $R^4$ independently are hydrogen or lower alkyl.

7. A compound of claim 1, wherein Z is

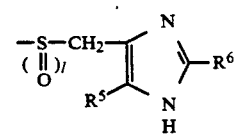

in which $l$ represents an integer from 0 to 2, and $R^5$ and $R^6$ independently are hydrogen or lower alkyl.

8. A compound of the formula (I):

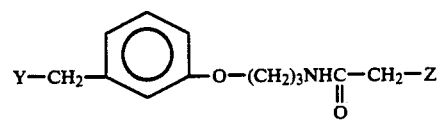

in which Y is piperidino, 1-pyrrolidinyl, or 3-hydroxy-1-pyrrolidinyl, and Z is

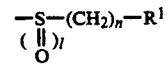

in which $l$ represents an integer from 0 to 2, n represents an integer from 1 to 3, $R^1$ is hydroxy, 1,2-dihydroxyethyl, 1-hydroxyethyl, 2-phenoxy-1-hydroxyethyl, 2-hydroxyethoxy, lower alkoxycarbonyl, 2,2-dimethyl-1,3-dioxolan-4-yl, or lower acyloxymethyl; or a salt or cyclodextrin inclusion compound thereof.

9. N-[3-[3-(piperidinomethyl)phenoxy]propyl]-2-(2-hydroxyethyl-1-thio)acetamide.

* * * * *